United States Patent
Vignery et al.

(10) Patent No.: US 8,852,240 B2
(45) Date of Patent: Oct. 7, 2014

(54) METHODS AND COMPOSITIONS FOR FOSTERING AND PRESERVING BONE GROWTH

(75) Inventors: Agnès Vignery, Branford, CT (US);
Nozer M. Mehta, Randolph, NJ (US);
James P. Gilligan, Union, NJ (US);
Kieran P. Murphy, Baltimore, MD (US)

(73) Assignees: Kieran Murphy, LLC, Towson, MD (US); Yale University, New Haven, CT (US)

( * ) Notice: Subject to any disclaimer, the term of this patent is extended or adjusted under 35 U.S.C. 154(b) by 0 days.

(21) Appl. No.: 11/796,439

(22) Filed: Apr. 27, 2007

(65) Prior Publication Data

US 2008/0213333 A1    Sep. 4, 2008

Related U.S. Application Data

(63) Continuation-in-part of application No. 11/254,640, filed on Oct. 21, 2005.

(60) Provisional application No. 60/621,060, filed on Oct. 25, 2004.

(51) Int. Cl.
| | |
|---|---|
| *A61B 17/88* | (2006.01) |
| *A61F 2/46* | (2006.01) |
| *A61L 27/54* | (2006.01) |
| *A61L 27/12* | (2006.01) |
| *A61B 17/58* | (2006.01) |
| *A61B 17/56* | (2006.01) |

(52) U.S. Cl.
CPC ........... *A61B 17/58* (2013.01); *A61L 2300/414* (2013.01); *A61L 27/54* (2013.01); *A61L 27/12* (2013.01); *A61L 2300/112* (2013.01); *A61L 2300/43* (2013.01); *A61L 2300/252* (2013.01); *A61B 2017/564* (2013.01)
USPC ........................................ 606/279; 606/86 R

(58) Field of Classification Search
USPC .......... 623/11.11, 13.12, 17.17, 16.11, 17.11, 623/18.11, 22.11; 514/21; 435/810; 606/60, 606/62, 76, 77, 86, 92–94, 87, 88, 89, 90, 606/91, 95
See application file for complete search history.

(56) References Cited

U.S. PATENT DOCUMENTS

| | | | |
|---|---|---|---|
| 2002/0187104 A1* | 12/2002 | Li et al. ........................... | 424/44 |
| 2003/0212426 A1 | 11/2003 | Olson, Jr. et al. | |

(Continued)

FOREIGN PATENT DOCUMENTS

| | | |
|---|---|---|
| CA | 2518104 | 2/2013 |
| JP | 2003-530151 | 10/2003 |

(Continued)

OTHER PUBLICATIONS

U.S. Appl. No. 11/254,640, filed Oct. 21, 2005, Murphy et al.

(Continued)

*Primary Examiner* — Sameh Boles
(74) *Attorney, Agent, or Firm* — F. Chau & Associates, LLC

(57) ABSTRACT

A method for augmenting bone in a subject in need thereof including installing within an interior portion of a bone located in the subject a sufficient amount of a biocompatible material to form a scaffold within the bone interior, wherein the scaffold serves as a support for the formation of new bone within the bone interior portion, and administering to the subject a sufficient amount of at least one bone augmentation agent to elevate blood concentration of at least one anabolic agent in the subject. The method may further include administering at least one anti-resorptive agent to the subject in an amount sufficient to substantially prevent resorption of new bone growth. In another embodiment, the method may further include a step of mechanically inducing an increase in osteoblast activity in the subject, wherein the elevation in blood concentration of the anabolic agent and the increase in osteoblast activity at least partially overlap in time.

26 Claims, 10 Drawing Sheets

(56) References Cited

U.S. PATENT DOCUMENTS

| | | | |
|---|---|---|---|
| 2005/0119662 | A1 | 6/2005 | Reiley et al. |
| 2005/0256047 | A1* | 11/2005 | Vignery et al. ............... 514/12 |
| 2006/0089723 | A1 | 4/2006 | Murphy |
| 2007/0041906 | A1* | 2/2007 | Lidgren et al. ............... 424/9.4 |

FOREIGN PATENT DOCUMENTS

| | | |
|---|---|---|
| JP | 2004511320 | 4/2004 |
| JP | 2005506114 | 3/2005 |
| JP | 2005508217 | 3/2005 |
| JP | 2005519067 | 6/2005 |
| JP | 2006-263184 | 10/2006 |
| WO | 01/76514 A2 | 10/2001 |
| WO | 02/32827 | 4/2002 |
| WO | 02080933 | 10/2002 |
| WO | 02/098474 | 12/2002 |
| WO | 2004078223 | 9/2004 |
| WO | 2005112864 | 12/2005 |
| WO | WO 2005/112864 | 12/2005 |
| WO | 2006/014886 | 2/2006 |
| WO | WO 2006/072622 | 7/2006 |
| WO | PCT/US06/032242 | 8/2006 |
| WO | 2006124708 | 11/2006 |
| WO | 2007038009 | 4/2007 |
| WO | PCT/US07/63766 | 12/2007 |

OTHER PUBLICATIONS

U.S. Appl. No. 11/267,987, filed Nov. 7, 2005, Vignery et al.
U.S. Appl. No. 11/128,095, filed May 11, 2005, Vignery et al.
U.S. Appl. No. 11/430,752, filed May 9, 2006, Vignery et al.
International Preliminary Report on Patentability dated Nov. 15, 2009 corresponding to International Patent Application No. PCT/US2007/010267.
Canadian Office Action dated Jun. 2, 2011 in corresponding Canadian Patent Application No. 2,582,846.
First Office Action dated Jan. 18, 2012 issued in corresponding Chinese Appln. No. 200780052739.5.
Skripitz R., et al. "Strong effect of PTH (1-34) on regenerating bone: A time sequence study in rats", ACTA Orthopaedica Scandinavica, Munksgaard, Copenhagen, DK, vol. 71, No. 6, Dec. 1, 2000, pp. 619-624.
Skripitz R., et al. "Parathyroid horomone (1-34) increases attachment of PMMA cement to bone", Journal of Orthopaedic Science, Springer Verlag. Tokyo, JP, vol. 6, No. 6, Jan. 1, 2001, pp. 540-544.
European Search Report dated May 7, 2012 issued in corresponding European Appln. No. 07776368.8.
English Abstract for Corresponding Document: WO03024316 (for JP2005508217).
English Abstract for Corresponding Document: WO03061690 (for JP2005519067).
English Translation of Japanese Office Action Dated Apr. 3, 2012.
Kenny, J Mater Sci Mater Med, 14(11), pp. 923-938, Nov. 2003 (Abstract Only).
Canadian Office Action dated Dec. 6, 2012 in corresponding Canadian Appln. No. 2,582,846.
English Translation of Japanese Final Decision for Rejection dated Nov. 27, 2012 in corresponding Japanese Appln. No. 2010-506155.
Office Action dated Feb. 12, 2014 issued by the Japanese Patent Office in corresponding Japanese Application No. 2010-506155 (with English Translation).
Office Action dated Mar. 10, 2014 issued by the Canadian Intellectual Property Office in corresponding Canadian Application No. 2,685,407.

\* cited by examiner

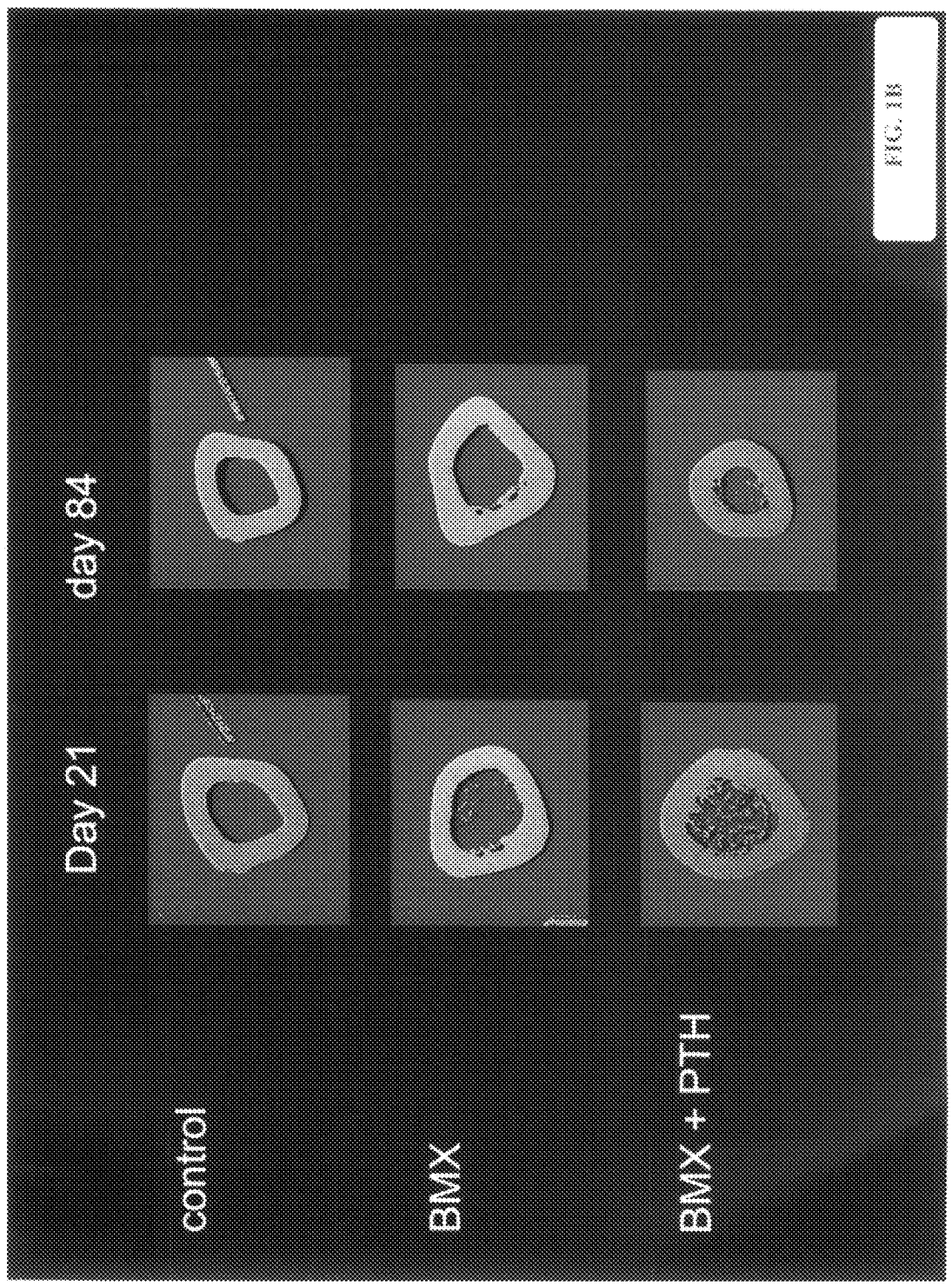

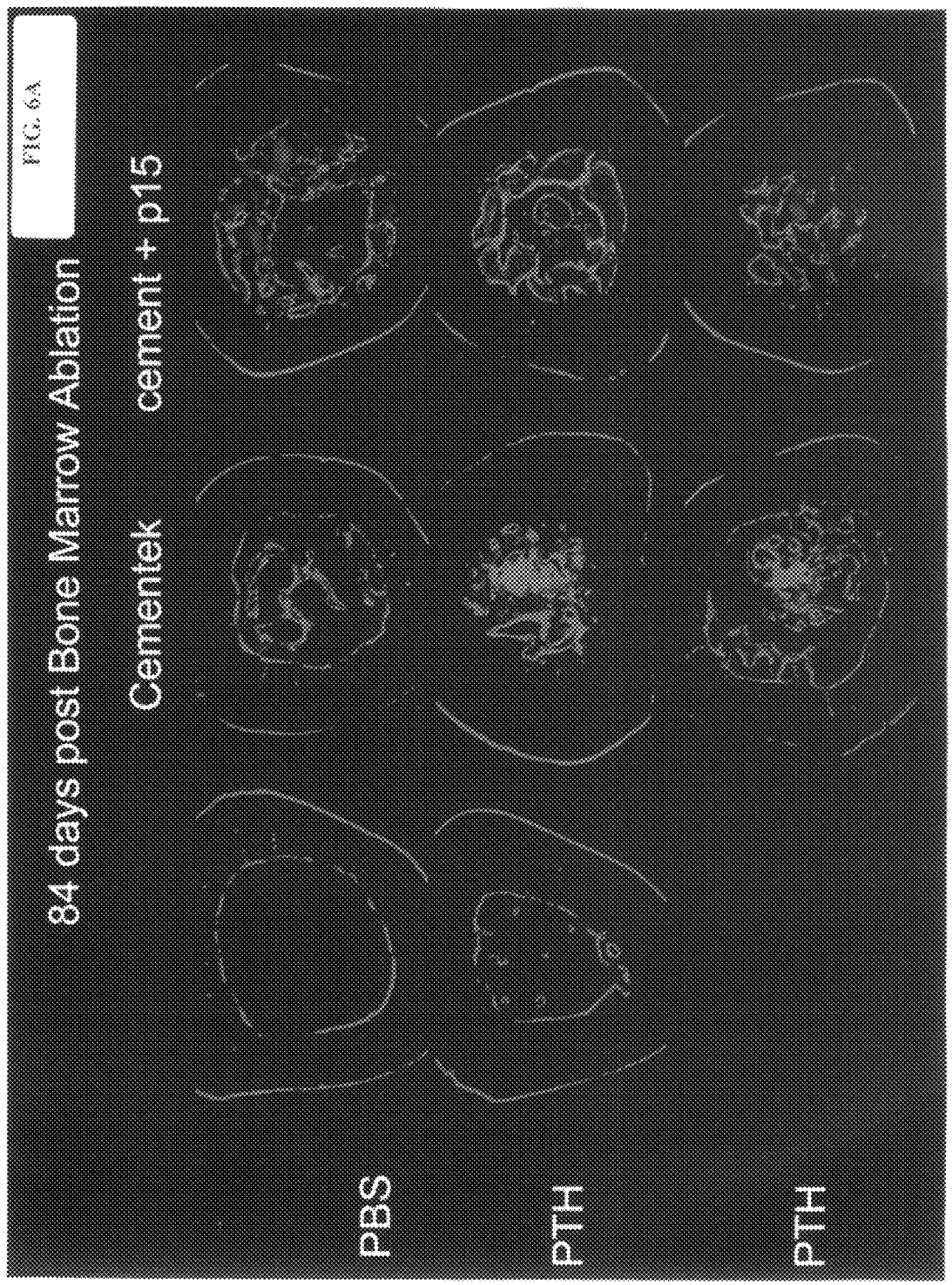

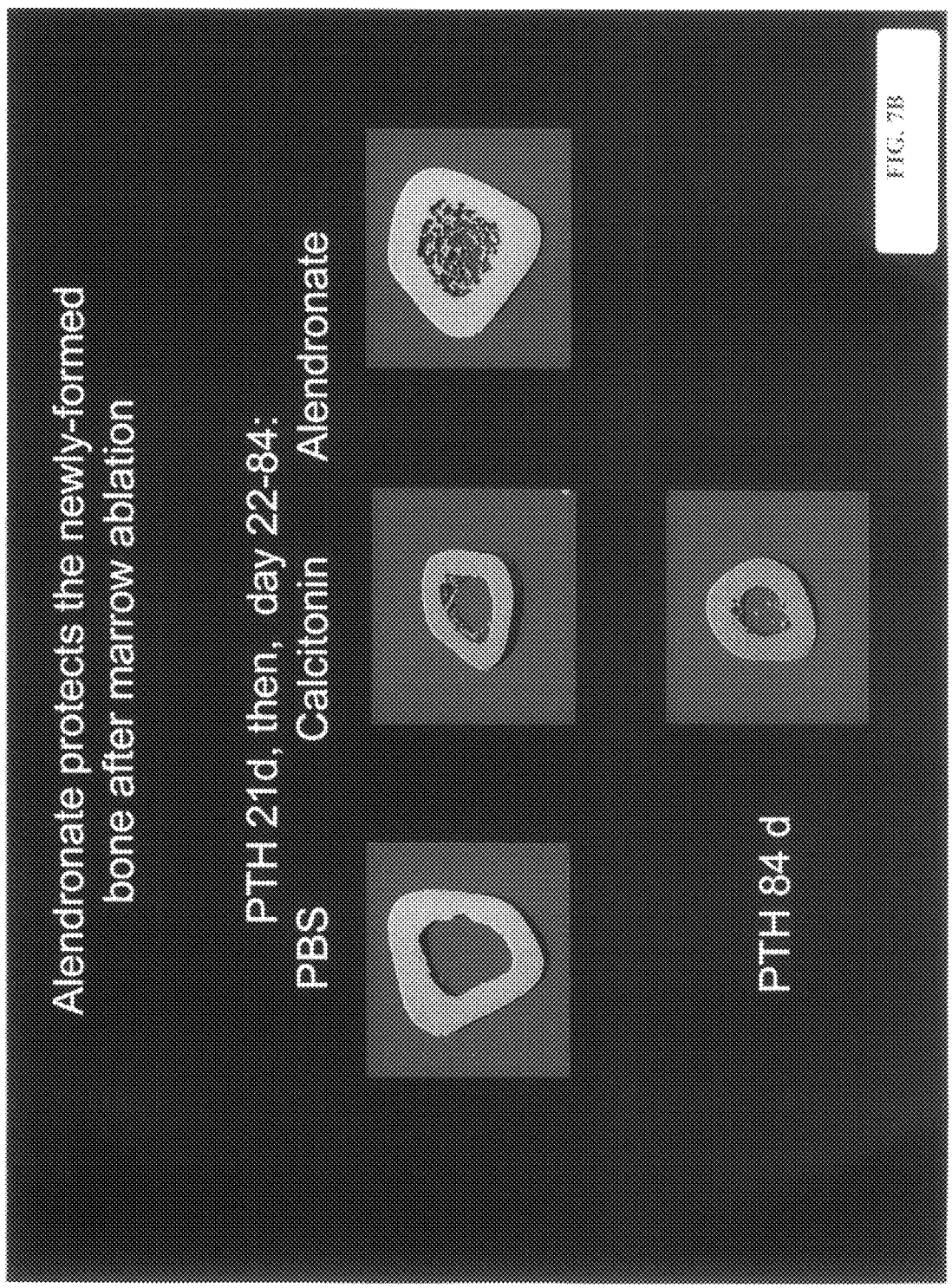

METHODS AND COMPOSITIONS FOR FOSTERING AND PRESERVING BONE GROWTH

CROSS-REFERENCE TO RELATED APPLICATIONS

This application is a Continuation-in-Part of and claims the priority of pending application Ser. No. 11/254,640 of Kieran P. Murphy filed Oct. 21, 2005, which claims the priority of U.S. Provisional Application No. 60/621,060, filed Oct. 25, 2004. The disclosure of both the above applications are expressly incorporated by reference into this application.

FIELD OF THE INVENTION

The present invention relates generally to methods and compositions for fostering and preserving bone growth in a subject. More particularly, the invention comprises inducing rapid bone formation at locations such as the site of a bone fracture; in areas within the skeleton having diminished bone density; and/or in areas such as the portion of long bones lacking cancellous bone structure and thereafter preserving the new bone thus formed while fostering the growth of additional bone at any such location by, inter alia, providing an internal framework or scaffolding upon which newly produced bone may fasten and grow. Anti-resorption agents may optionally be administered for purpose of reducing the resorption over time of the newly formed bone.

BACKGROUND OF THE INVENTION

The bones of the skeleton are not entirely solid throughout. The outside, i.e., cortical, bone is substantially solid, having only a few small (Haversian) canals. Located inwardly from the cortical bone, however, is spongy bone known as cancellous (or trabecular) bone. The cancellous bone is composed of a honeycomb network of trabecular bone defining a plurality of spaces or cavities filled with fluid bone marrow, stem cells and some fat cells. Existing within these bone marrow cavities are, inter alia, various highly specialized cells which assist in breaking down existing bone (i.e., osteoclasts) as well as cells that correspondingly produce new bone (i.e., osteoblasts) to replace that which is broken down or which may be otherwise lost due to factors such as injury or illness.

As indicated above, the physical structure of bone may be compromised for a variety of reasons, including injury and disease. One of the most common bone diseases is osteoporosis, which is characterized by low bone mass and structural deterioration of bone tissue, leading to bone fragility and increased susceptibility to fractures, particularly of the hip, spine and wrist. Osteoporosis develops where there is an imbalance such that the rate of bone resorption exceeds the rate of bone formation. This is, in part, due to the fact that it can require six months for osteoblasts to rebuild the amount of bone destroyed by osteoclasts in three days. By age fifty-five, for example, the average woman with osteoporosis has already lost thirty percent of her bone mass.

Osteoporosis is drastically accelerated during menopause and is the third leading cause of death of women over seventy. The disease also afflicts men, who account for twenty percent of all osteoporosis sufferers. By the age of seventy-five, approximately ninety percent of all women and thirty-three percent of all men will suffer from osteoporosis. The ailment causes 1.5 million fractures a year, resulting in annual U.S. health care costs exceeding $18 billion. One in two women and one in eight men over age fifty will have an osteoporosis-related fracture in their lifetime. Of those who suffer from hip fractures, one in five will not survive more than one year. Currently, less than ten percent of afflicted persons are treated for osteoporosis with prescription drugs.

Such prescription drugs typically include at least one bone augmentation agent. A 'bone augmentation agent', as that term is used herein, includes but is not limited to bone anabolic agents, and agents that cause elevated blood levels of an endogenous bone anabolic agent to be produced within a subject. Bone augmentation agents, such as bone anabolic agents, are well known in the art. Bone anabolic agents commonly include (but are not limited to) parathyroid hormone and various parathyroid hormone fragments, whether amidated or in the free acid form, as well as PTHrP and analogues thereof, Prostaglandin E-2, Bone Morphogenic Proteins, IGF-1, Growth Hormone, fibroblast growth factor TGF and others. On the other hand, agents causing increased expression of endogenous bone anabolic agent include, but again are not limited to, calcilytic agents as well as antibodies to sclerostin. Calcilytic agents typically, but not necessarily, include agents that limit the binding of calcium to its receptor, thereby triggering the release of endogenous parathyroid hormone. Examples of these materials are set forth in U.S. Pat. Nos. 6,362,231; 6,395,919; 6,432,656 and 6,521,667, the contents of which are expressly incorporated herein by reference.

Reliance upon the administration of bone augmentation agents such as those described above, for the purpose of, e.g., increasing bone density, however, frequently involves lengthy treatment regimens with accompanying patient compliance problems. Additionally, such treatment produces a systemic effect which targets the entire skeletal system and thus, it is not and can not be 'targeted' to create an effect in one or more specific bone(s).

In order, therefore, to provide a faster and more targeted method of inducing bone formation in subjects suffering from, e.g., diminished bone mass, and for aiding in preserving the retention of the new bone growth so produced, several of the co-inventors of the present invention have developed a method for fostering bone formation and preservation which overcomes the deficiencies noted above of the prior art. The method comprises the steps of mechanically inducing an increase in osteoblast activity in one or more 'targeted' bones of a subject in need of additional bone growth, coupled with elevating blood concentration of at least one bone anabolic agent in the subject, wherein the above steps may be performed in any order but wherein they are carried out in sufficient time proximity that the elevated concentration of the bone anabolic agent and the mechanically induced increase in osteoblast activity at least partially overlaps. The above methodology is described, for example, in U.S. patent application Ser. No. 11/128,095 file May 11, 2005 and in U.S. continuation-in-part patent application Ser. No. 11/267,987 filed Nov. 7, 2005. The contents of both of these applications are incorporated herein by reference. As indicated above, the method permits specific targeting of particular bones for effects such as repair, strengthening, reshaping and/or remodeling.

Although the above-described method has been found to be particularly effective in growing and preserving new bone when the area targeted for such additional bone growth is provided with a sufficient amount of cancellous bone to serve as a scaffold for supporting the new growth, it has now been determined that the new bone produced by the action of the bone anabolic agent alone, whether such agent is endogenous or otherwise, may not be ideal for replacement of bone in regions which lack sufficient cancellous bone to serve as a scaffold. Furthermore, the use of PTH and other anabolics may not be efficient at filling gaps in trabeculae that are perforated due to increased bone resorption. Over time, some of the bone produced via augmentation agents (including but not limited to anabolic agents) may be lost via such resorption in those areas, as noted above, lacking the bony scaffolding. Previous efforts to prevent, or at least minimize such resorption, have involved the administration of anti-resorptive agents, which are well-known in the art. These agents include (but are not limited to) calcitonins including, for example, human calcitonin, salmon calcitonin, eel calcitonin, elkatonin, porcine calcitonin, chicken calcitonin, SERMS (Selective Estrogen Receptor Modulators), Bisphosphonates, Strontium Ranelate and combinations thereof. Such administration of an antiresorptive agent is able to protect the newly formed bone. However, some or all of the new bone formed during the initial growth 'spurt' facilitated due to the presence of the anabolic agent, may nevertheless be resorbed by the subject. Thus, the effectiveness of the new bone, such as increased skeletal strength and/or support, will be compromised.

It has been discovered, however, by the present inventors that the addition of a biocompatible matrix-forming material in these specific areas will prevent the new targeted bone from being lost since it will serve as a support permitting additional bone growth. In addition, the installation of such a biocompatible matrix has been found to better enable bone to be synthesized in regions such as the area within the shaft of a long bone, e.g., the humerus.

For purposes of illustration, one particular location where bone thinning and resultant bone damage, including fracturing, attributable to such thinning is problematic is in the vertebrae of the spine. Vertebroplasty and kyphoplasty, which are currently in common use in the United States, are surgical procedures for vertebral augmentation that also treat pain associated with vertebral compression fractures. Both of these procedures use x-ray guidance and a transpedicular or parapedicular technique to access the vertebral body for injecting liquid cement therein. The cement then solidifies to augment the weakened and painful vertebra. The simplest procedure is vertebroplasty. This technique is discussed, for example, in U.S. Pat. No. 6,273,916, the contents of which are incorporated herein by reference. A more recent procedure, becoming more common, is kyphoplasty which involves the inflation of a balloon to restore height, whereupon a bone cement is injected into the cavity created by the balloon.

A highly popular bone cement for use in these procedures is polymethyl methacrylate ("PMMA"). The use of PMMA is described in a variety of professional journal articles, including: (a) "Is Percutaneous Vertebroplasty without Pretreatment Venography Safe? Evaluation of 205 Consecutive Procedures", Cristiana Vasconcelos, Philippe Gailloud, Norman J. Beauchamp, Donald V. Heck, and Kieran J. Murphy, AJNR Am J Neuroradiol 23:913-917, June/July 2002 ("Vasconcelos"); (b) "Bone Cements: Review of Their Physiochemical and Biochemical Properties in Percutaneous Vertebroplasty", Matthew J. Provenzano, Kieran P. J. Murphy, and Lee H. Riley III, AJNR Am J Neuroradiol 25:1286-1290, August 2004 ("Provenzano"); (c) "The Chemistry of Acrylic Bone Cements and Implications for Clinical Use in Image-Guided Therapy", David A. Nussbaum, M S, Philippe Gailloud, Md., and Kieran Murphy, Md., J Vasc Interv Radiol 2004; 15 Page 1. ("Nussbaum"). The contents of each of these papers is incorporated herein by reference.

PMMA is an acrylic bone cement. It is not adhesive and it does not integrate into bone over time, and yet it is remarkably strong. As an analogy, PMMA can act like rebar in cement as used in building construction. The use of PMMA does offer a significant drawback, however, in that PMMA is known to remove or reduce forces that maintain bone density by supplanting the role of trabecular bone structure in its neighborhood, thus removing or reducing the electrical charge that contributes to bone development.

Furthermore, the monomer liquid used to dissolve the PMMA powder can be toxic and has been associated with complications such as death and cardiac arrest (See the Nussbaum article). The high compressive strength of PMMA can, in addition, cause adjacent vertebral body fractures by exerting high non compliant forces on the adjacent vertebra, as the vertebral body is too stiff as a result of the injection of the PMMA. These adjacent fractures occur between eight and ten percent of the time.

A promising alternative to PMMA are biologically active bone cements or biocompatible polymers. Biologically active bone matrices can obviate some of the difficulties encountered with the use of PMMA. For example, biologically active bone cements can be of lower strength than PMMA, thus causing less stiffness of the vertebral body when they are injected. However, there are a number of problems inherent in their use in, for example, vertebral augmentation. For example, biologically active bone cements are very difficult to inject, they lack natural radio density, and they do not always integrate well for months or even years. Further, some biologically active bone cements require hours before they solidify and become safe. More generally, there have been deaths from the use of some of these cements, which may be related to the pH from the cement injected or the leaking of calcium into the circulation, resulting in disseminated clotting. There is currently little knowledge, however, of how to use biologically active bone cement for vertebral augmentation procedures.

A biologically active cement useful in vertebral augmentation is calcium phosphate. Calcium phosphate cements are composed of a powder and a liquid solution that dissolves the powder. They are used widely in hip, spine and wrist surgery and also in cranial restriction. There are two different families of calcium phosphate cements. One group undergoes an exothermic reaction while another undergoes an endothermic reaction. One group belongs to a family called bruschite cements. The other group belongs to a family that ultimately forms hydroxy apatite, the precursor of bone. When calcium phosphate powders and the aqueous solution are mixed, a paste is formed which sets within minutes to hours. Thus, they are often poorly injectable and poorly visualized under x-ray guidance, making them difficult to use for vertebral augmentation procedures. Further, when they are delivered into the bone, they are acted upon by osteoblasts and osteoclasts in the residual trabecular bone structure. If there is no residual trabecular bone structure the peripheral bone cement may be integrated at the endosteal surface of the bone, but bone cement located within the mass of the vertebral body may remain in its unchanged form, a brittle ceramic of low tensile and compressive strength with potential long term negative consequences.

In view of the deficiencies noted above of the prior art, there has been a long-felt need by those working in this field for a faster and more effective method of inducing bone formation in bones lacking a bony scaffolding comprised of trabecular bone, coupled with an enhancement in the degree of retention of the new bone thus produced. The present invention, in the manner set forth below, admirably fulfills these desired functions.

SUMMARY OF THE INVENTION

It is, therefore, an object of the present invention to provide novel and unobvious methods for inducing relatively rapid, targeted bone growth at all locations in need thereof while preserving and augmenting the new bone growth thus obtained.

Generally speaking, and as described in further detail below, the present invention provides a method of introducing a biocompatible material formed from a biologically active cement or other matrix-forming material within an inner portion of a bone and triggering new bone growth in the region, thereby integrating the cement or other matrix material together with the new bone into the existing bone architecture. In one embodiment of the invention, the removal of stromal cells via, e.g., irrigation, serves as a stimulus for targeted new bone growth, wherein a bone augmenting composition such as a bone anabolic agent prolongs the response, and wherein the matrix-forming material fills in voids where trabecular bone is lacking within an inner portion of the bone and serves as a scaffolding for new bone growth in regions lacking a sufficient amount of such trabecular bone, as well as in areas entirely lacking such trabecular bone. For example, a cyclic treatment paradigm of bone marrow irrigation coupled with administration of an anabolic agent in conjunction with the installation, within an interior portion of a bone, of a biocompatible matrix, followed by anti-resorptive therapy, is envisioned in accordance with the present invention.

The present invention thus provides, in one embodiment, a method for augmenting bone in a subject in need thereof wherein the method comprises installing within an interior portion of a bone within the subject a sufficient amount of a biocompatible material to form a scaffold within the bone interior, the scaffold serving as a support for the formation of new bone within the bone interior portion; and, administering to the subject a sufficient amount of at least one bone augmentation agent to elevate blood concentration of at least one anabolic agent in the subject.

In another embodiment, the invention provides a method for augmenting bone in a subject in need thereof wherein the method comprises mechanically inducing an increase in osteoblast activity within the subject; installing within an interior portion of a bone within the subject where the increase in osteoblast activity has been induced a sufficient amount of a biocompatible material to form a scaffold within the bone interior, the scaffold serving as a support for formation of new bone within the bone interior portion; and administering to the subject a sufficient amount of at least one bone augmentation agent to elevate blood concentration of at least one bone anabolic agent in the subject, wherein the elevation in blood concentration of the bone anabolic agent in the subject and the increase in osteoblast activity therein at least partially overlap in time.

In a further embodiment, the invention is directed to a kit for fostering and preserving bone growth in an interior portion of a bone lacking a sufficient trabecular scaffolding to substantially prevent resorption of new bone formed therein. The kit comprises at least one container having therein at least one biocompatible material adapted for forming an additional amount of scaffolding within the inner bone portion; and, at least one container having therein a bone augmentation agent.

In a further embodiment the invention is directed to a kit for fostering and preserving bone growth in an interior portion of a bone lacking a sufficient trabecular scaffolding to substantially prevent resorption of new bone formed therein. The kit comprises at least one container having therein at least one biocompatible material adapted for forming an additional amount of scaffolding within the inner bone portion; at least one container having therein a bone augmentation agent; and, a mechanical alteration device for altering contents of a bone marrow cavity in at least one targeted bone.

BRIEF DESCRIPTION OF THE FIGURES

The present invention will now be explained, by way of example only, with reference to certain embodiments and the attached Figures, in which:

FIG. 1B depicts the results from the same groups of animals using the imaging technique known as Micro-CT. This technique provides a high resolution analysis of the femoral shaft marrow cavity from the Control, BMX, and the BMX+ PTH 1-34 $NH_2$ of rats treated with PBS (buffer) or PTH for 21 or 84 days, respectively;

FIG. 6A illustrates the degree of persistent bone growth achieved after 84 days with the administration of a biocompatible material, in this instance Cementek (Cementek LV, Non-stoichiometric hydroxyapatite prepared from the reaction between the acid and base calcium phosphates in the presence of an aqueous solution. Teknimid, 65500 VIV en Biggore, France) or Pepgen-15 (a high purity anorganic bovine graft material, radiopaque, peptide-enhanced to mimic autogeneous bone. Dentsply Friadent CeraMed Lakewood, Colo.). All samples were taken from femurs which had BMX performed on them. The groups included: BMX followed by 84 days anabolic agent or PBS (buffer) presented in the first row or BMX followed by insertion of a slurry of biocompatible matrix (Cementek or Pepgen-15) with our without concomitant PTH treatment for 84 days;

FIGS. 7A and 7B illustrate the effect attributable to administration of the anti-resorption agent, Alendronate, in preserving bony tissue formed according to the method of the invention. The following treatment modalities are included: (a) BMX+PTH 1-34 $NH_2$ for 21 days+PBS (buffer) during days 22-84; (b) BMX+PTH 1-34 $NH_2$ for 21 days+calcitonin during days 22-84; (c) BMX+PTH 1-34 $NH_2$ for 21 days+Alendronate during days 22-84; and (d) BMX+PTH 1-34 $NH_2$ during days 1-84.

FIG. 7B depicts the results from the same groups of animals reported in FIG. 7A using the Micro-CT imaging technique, which provides a high resolution analysis of the femoral shaft marrow cavity.

DETAILED DESCRIPTION OF PREFERRED EMBODIMENTS OF THE INVENTION

As has been pointed out above in the discussion concerning the background of the present invention, it has been determined by the inventors that newly formed bone produced by the action of bone augmentation agent(s), such as a bone anabolic agent (e.g., parathyroid hormone), in areas lacking cancellous bone may not be permanent in nature and such bone may, in fact, become at least partially resorbed if constant anabolic therapy (alone) is applied. To address this issue, the invention describes two distinct approaches for preserving new bone in marrow cavities lacking such cancellous bone 'scaffolding', i.e., the cycling of a potent antiresorptive agent, such as a bisphosphonate or the inclusion of one or more biocompatible material such as (but not limited to) a biocompatible bone cement to serve as such scaffolding for supporting the new bone growth and fostering its maintenance.

For purposes of convenience in explaining the invention, the materials for forming a scaffolding within a targeted bone for facilitating bone growth according to the present invention are commonly referred to hereafter as "biocompatible materials" and/or "biologically active materials". This term is herein defined to include not only bone cements (including biocompatible bone cements) but also alternate materials, such as polymers, gels and/or foams, slurries or suspensions of calcium phosphate or hydroxyapatite now know or subsequently discovered, which provide the capability for forming the required scaffolding within the interior portion of the bone.

It is additionally to be understood that, in regions having sufficient amounts of cancellous bone to provide the scaffolding effect, the combination of a mechanical inducement of an increase in osteoblast activity, e.g., via bone marrow irrigation, coupled with the administration of a bone augmentation agent such as a bone anabolic agent, is sufficient to maintain new bone growth during the course of the treatment with the anabolic. However, in bones where the trabecular microarchitecture is either lacking (see, e.g., FIGS. 1A and 1B) or has been compromised and/or wherein numerous trabeculae have been perforated, the inclusion of biocompatible materials—coupled with the aforementioned bone marrow irrigation and anabolic treatment—improves the overall bone augmentation and maintenance. Bone resorption in the diaphysis of long bones lacking cancellous bone architecture has been found to occur even in those instances where the administration of, e.g., bone anabolic agent is coupled with the inducement of increased osteoblast activity in a bone targeted for such additional bone growth, which technique is described, for example in application Ser. No. 11/128,095 filed May 11, 2005 and application Ser. No. 11/267,987 filed Nov. 7, 2005 which are incorporated above by reference into this application.

Figure 1A:
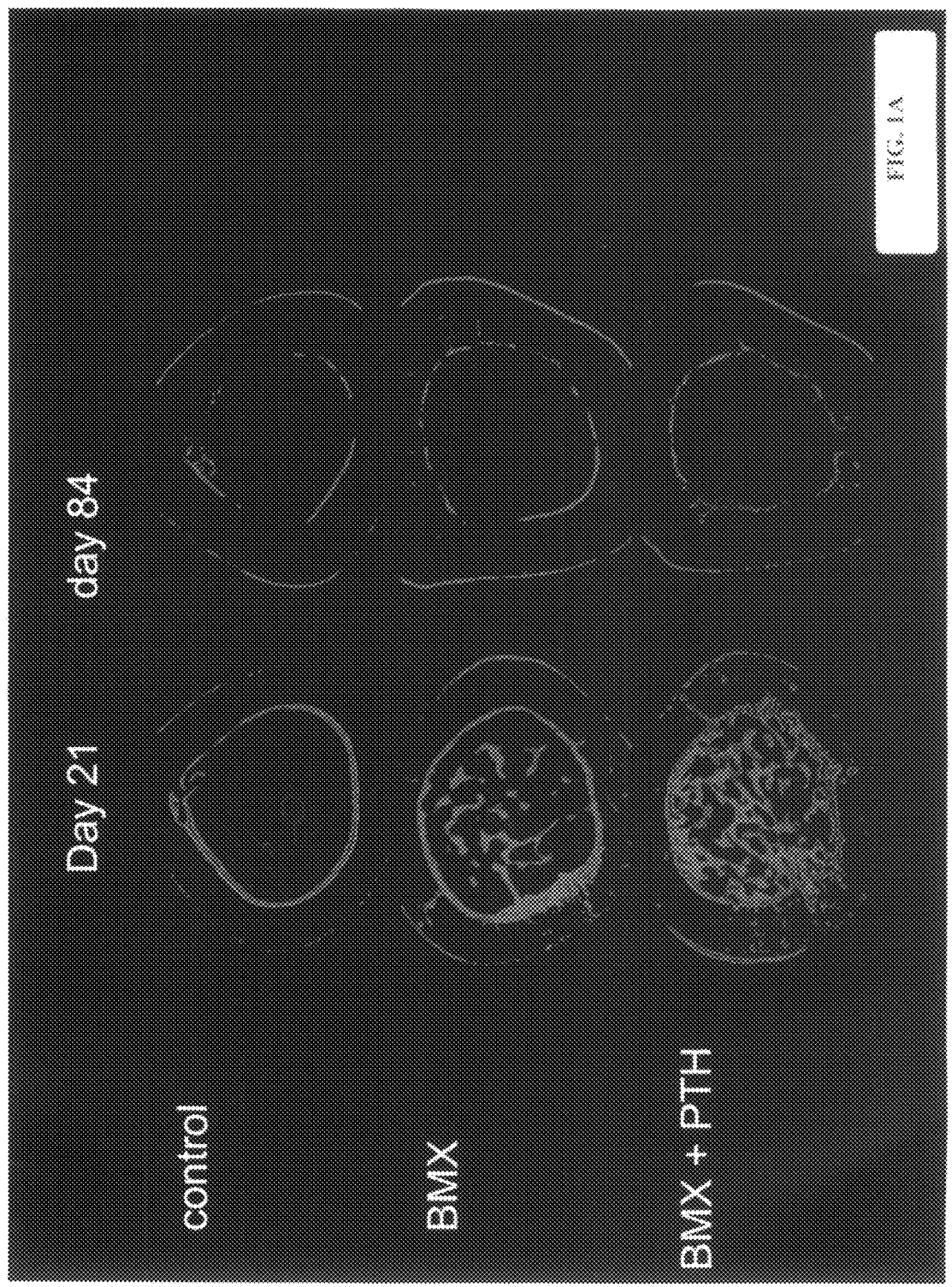
FIG. 1A is a section of the mid-shaft of a rat femur following, respectively, 21 and 84 days of treatment. The groups include: (a) control—no bone marrow ablation ("BMX") or anabolic agent, (b) BMX—bone marrow ablation alone; and (c) BMX+PTH–bone marrow ablation plus treatment for either 21 or 84 days with PTH 1-34 $NH_2$. In addition, the rats were injected with calcein, a fluorescent dye, on 9, 8, 2 and 1 day prior to sacrificing the animals. Calcein becomes incorporated into bone and serves as a measure of bone growth and mineralization.

As shown for example in FIG. 1A, treatment with PTH for 21 days extends the bone-formation phase that follows BMX and leads to additional bone formation. At day 84, bone remodeling has taken place, resulting in the resorption of a substantial portion of the bone that was present at day 21 in the BMX and BMX+PTH groups. These results suggest that in regions of bone lacking the cancellous bone network (i.e., scaffolding), resorption occurs over time.

In reviewing FIG. 1B, one notes the abundance of newly formed bone in the marrow cavity as a result of BMX at Day 21, which is further augmented by treatment with PTH for 21 days. By contrast, the marrow cavity from the mid-shaft of BMX-treated femurs from rats treated with PBS or PTH for 84 days is no longer undergoing bone formation and, indeed, no longer contains substantial amounts of bone. These results confirm the observations obtained with calcein labeling as shown in FIG. 1A.

Although, as indicated above, bone resorption may be slowed and/or reduced via the administration of an anti-resorptive agent, such as calcitonin and/or alendronate, it remains desirable for obvious reasons to diminish if not entirely eliminate bone loss to the degree possible, as is accomplished with the use of the methods and compositions according to the present invention which is useful with long bones, hips, spines and, in fact, any bone lacking (or having a diminished) cancellous bone network. The present invention, thus, provides methods and compositions for achieving rapid and sustained targeted bone growth, coupled with a desirable reduction in loss of the new bone thus produced due to factors such as resorption in particular targeted areas of bone.

Figure 2:
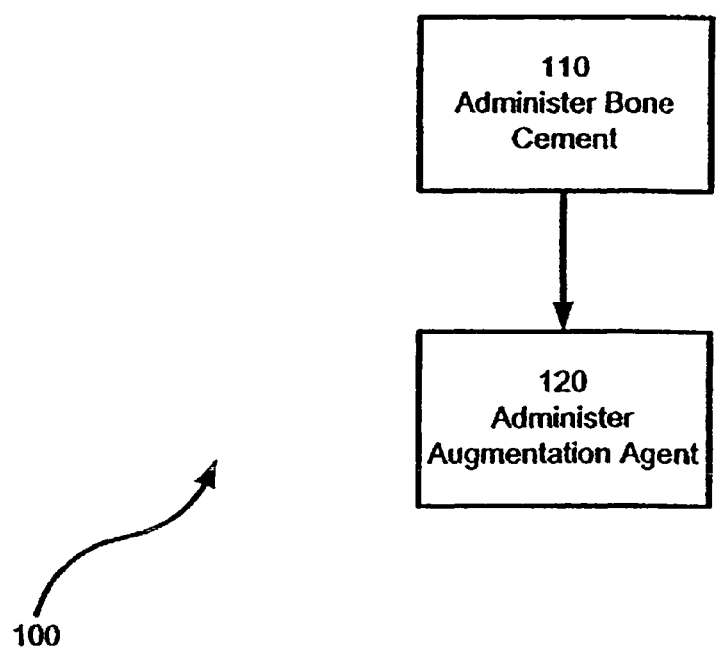
FIG. 2 is a flowchart for depicting a method for augmenting bone in accordance with one embodiment of the invention; the procedure entails the administration of a biocompatible matrix material, which may be but is not necessarily a biocompatible bone cement, in conjunction with the administration of a bone augmentation agent such as a bone anabolic formulation.

In one embodiment, illustrated at 100 in FIG. 2, the invention is directed to a method for augmenting a bone, including (but not limited to) long bones, e.g., the femur and humerus, as well as smaller bones, such as the vertebrae, of an individual. As the term is used herein, 'augment' or 'augmentation' means to increase the amount and/or density of bony tissue contained within the bone, while correspondingly reducing or preventing entirely if possible the subsequent accelerated resorption of the newly formed bony tissue produced with the use of the method.

The above is accomplished with the use of a method which comprises, in one step, imparting a biologically active material such as a bone cement into an interior portion of the bone to be augmented. The biocompatible material, including but not limited to a bone cement, can be delivered in a radiographically controlled way or by open surgical application. Various biocompatible materials which are effective for use in the method of the present invention are described more fully below.

The biologically active material associates with the trabecular bone structure located in an interior portion of a 'target' bone to form a scaffolding therein which serves as a framework for permitting additional bone growth at that location, so as to permit restoration of normal bone functionality and strength in a desired area, e.g., an area where a fracture has occurred or an area at risk for a future fracture due, e.g., to a loss of bone density. Over time in the presence of the anabolic agent the cement and newly formed bone become integrated into the existing bone structures. This is advantageous as normal trabecular bone has sophisticated weight distribution, compression shear strength and regenerative properties that cannot be reproduced with, for example, the use of bone cements alone.

In the present discussion, augmentation of vertebral bone is frequently relied upon as a means of exemplifying the invention. However, the invention is not to be construed as being limited to use only with vertebral bones. That is, as indicated above other bones can be augmented by means of the methodology described herein, including, but not limited to, the hip, the proximal femoral neck, the distal radius, the proximal humerus, the calcaneus, a rib or ribs, the tibia, and the sacrum.

Figure 3:
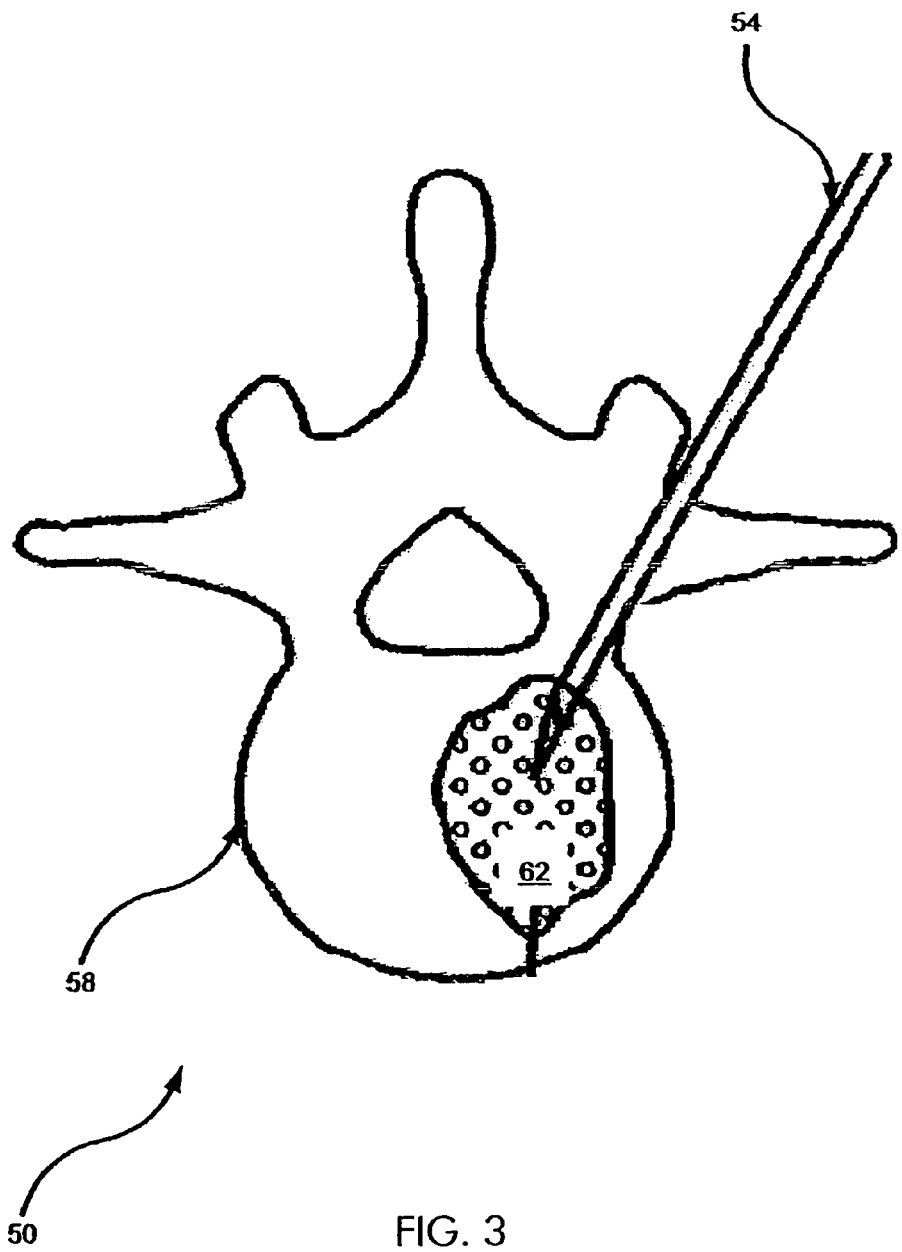
FIG. 3 represents an axial view of a vertebra having an osteoporotic fracture, wherein the vertebra is undergoing administration of a biocompatible matrix material (e.g., a biologically active bone cement) in the performance of one of the steps identified in FIG. 2. The biocompatible material is injected into a space devoid of cancellous bone to provide a scaffold for permitting persistent bone formation.

Referring now to FIG. 3 provided with this application, a vertebra is indicated generally at 50. Vertebra 50 has an osteoporotic fracture or a spinal deformity and exemplifies one type of bone and a corresponding condition (i.e., a fracture) that can be treated with the use of method 100. Thus, to treat vertebra 50 using method 100, step 110 is performed which comprises the administration of the biologically active material following irrigation for removing stromal cells. In certain instances, the introduction into the bone of the biocompatible material can serve as the method for removing the stromal cells, but the preferred method involves a preliminary irrigation to efficiently removal stromal cells bone marrow.

In the case of a vertebra such as vertebra 50, administration of the biocompatible material is typically performed using vertebroplasty or kyphoplasty. In FIG. 2, vertebra 50 is shown undergoing a vertebroplasty to effect step 110. The figure thus shows a vertebroplasty needle 54 inserted along a transpedicular approach, with the tip of needle 54 positioned within the vertebral body 58. The irrigation and removal of stromal cells can be accomplished using the same needle or a specifically modified needle that provides a better method for irrigation and collection of the stromal cells.

It should be understood that the performance of step 110 on vertebra 50 can be effected using any presently known or future contemplated vertoblasty techniques, using appropriate or desired needles, image guidance modalities and the like. The type of biocompatible material (e.g., bone cement) 62 will influence such choices and will also be selected as a means of complementing the choices used to effect step 120.

As still another means of implementing method 100, the administration of the biocompatible material and the augmentation agent may be achieved via separate injections into the vertebral body. Thus, the cement or other biocompatible matrix material may be injected into one pedicle of the vertebral body and the bone augmentation agent could be injected into the other pedicle or through an ipsilateral approach through the same pedicle as the biocompatible material or it may, instead, be mixed therewith. The anabolic agent can be administered systemically as well.

In the method of the invention described herein, it is contemplated that the biocompatible material is, in one embodiment of the invention, at least one biologic bone cement, also referred to herein as a biologically active bone cement. Suitable biocompatible materials include, but are not limited to calcium phosphate, calcium hydroxyapatite, calcium sulphate, calcium aluminate a bone morphogenic protein, polymers, fibrinogen, synthetic fibrins, collagen gels, collagen plus hydroxyapatite suspensions and various combinations thereof. Particular examples of these materials, provided only for the purpose of exemplifying (and not limiting) the invention, include, (a) Alpha-BSM Bone Substitute Material, comprising a synthetic bioresorbable bone substitute material engineered the chemical composition and crystalline structure of the crystalline structure of bone, sold by ETEX Corporation, Cambridge Mass.; (b) Cortoss Synthetic Cortical Bone, comprised of three di-functional cross-linked resins delivered as two mix-on-demand pastes, sold by Orthovita Corp., Malverne Pa.; (c) Cementek LV, a non-stoichiometric hydroxyapatite prepared from the reaction between acid and basic calcium phosphates in the presence of an aqueous solution, sold by Teknimid located at 65500 VIC en Bigorre, France; (d) Pepgen P-15, a high purity anorganic bovine graft material that is radiopaque and is peptide-enhanced to mimic autogenous bone, sold by Dentsply Friadent CereaMed Lakewood COP-P; and (e) Norian SRS (Skeletal Repair System), which is an injectable, moldable and biocompatible calcium phosphate which sets at body temperature into a carbonated apatite, sold by Synthes, Inc. located in West Chester, Pa.

It may be desired to select combinations of such materials where one or more cements provides, for example, short term stability and/or pain relief, while another provides long term integration and new bone development. The selection of the biomaterial will be site specific. For example, the biocompatible material used to prevent hip fractures will be different from the biomaterial used to support vertebrae during vertoplasty. Additionally, the biocompatible material, in most instances, will not be used in an "off the shelf" condition. That is, its formulation and/or physical state will be modified as necessary for a particular application, for example, by conversion into a suspension, foam or gel and/or by modifying factors such as the concentration, size, shape, etc. of the solid particles of which these materials are comprised.

Enhanced bone cements are also useful in the invention and include a bone cement as well as an augmentation agent. Examples of the bone cement used in such enhanced bone cements include Cementek and Cementek LV, while examples of the augmentation agent used in these enhanced bone cement include (but are not limited to) insulin related growth factor ("IGF"), rhPTH, GH, anabolic vitamin D analogs, low density lipoprotein receptor related protein 5 (LRP5) activator, or an inhibitor of sclerostin binding to LRP5, an activator of non genomic estrogen signaling (ANGELS), a bone morphogenic protein, a growth hormone releasing factor (GHRF) hepatcyte growth factor (HGF) calcitonin gene related peptide (CGRP) parathyroid related peptide (PTHrP) Transforming growth factor (TGF) and/or combinations thereof.

In accordance with the present invention the embodiment as described herein additionally constitutes a further step (i.e., performed in conjunction with the installation within a target bone of the biologically active bone cement), which involves the administration to the subject of a bone augmentation agent. It is envisioned that the bone augmentation agent will be administered to the subject on, e.g., a daily basis for up to six (6) months. The augmentation agent, such as a bone anabolic composition for example, assists by facilitating or otherwise enhancing the growth of trabecular bone upon the surface of a scaffolding formed by the bone cement and thereafter resulting in a diminished degree of bone resorption, at least in comparison to methods using either the bone cement or the bone augmentation agent by themselves. The bone augmentation agent can be administered in any suitable manner, including by injection, intravenously ("IV"), peroral ("PO"), transdermally, transnasally or transrectally and at any suitable time before, during or after the installation of the bone cement within the interior of the bone.

As indicated above, i.e., in accordance with the recitation of, for example, trans-dermal and nasal routes of administration, the agent may be administered systemically or else directly to a location where the bone cement is introduced. The timing and method of administration of the bone augmentation agent would be well understood by one having ordinary skill in this field of art. That is, the steps in method 100 can be performed in a different order than shown, or simultaneously. The bone augmentation agent can be, as indicated above, an anabolic bone agent or any other agent that promotes the integration of the injected cement. The bone augmentation agent has been found, as indicated above, to produce a joint effect with that provided by the bone cement which helps to convert the biologically active bone cement to actual bone more rapidly then is usually achieved in the poor quality trabecular bone of the osteoporotic patient. In the absence of the bone anabolic agent the bone cement can be resorbed, thus diminishing its effectiveness. Some useful bone augmentation agents are exemplified below.

Figure 4:
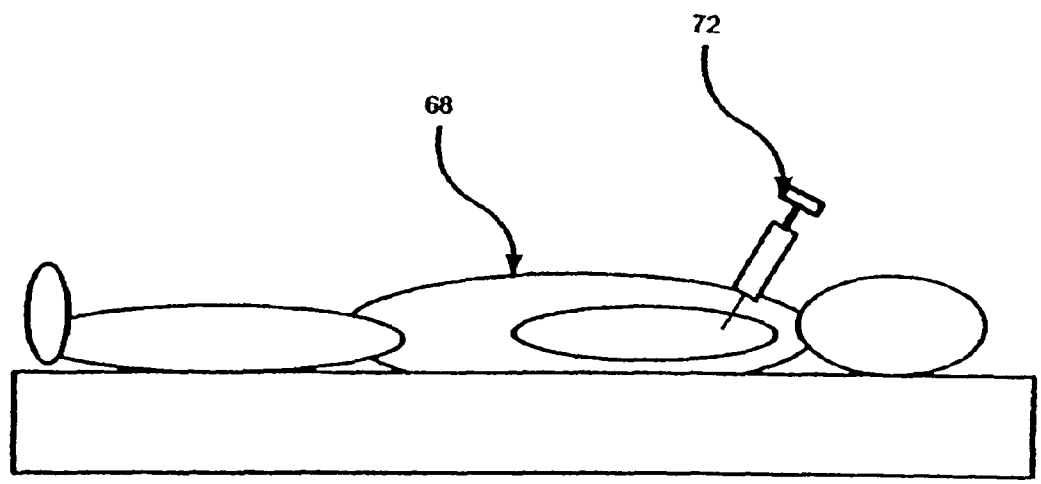
FIG. 4 is a representation of the administration of a bone augmentation agent, such as a bone anabolic agent, in the performance of one of the steps identified in FIG. 2. The biocompatible matrix may have an anabolic agent associated with or comingled with the matrix. In addition, the anabolic agent may, alternately, be systematically administered to the subject.

In a particular embodiment as shown for example in FIG. 4, a sufficient amount of one preferred bone anabolic agent, i.e., PTH[1-34]NH$_2$, is administered to patient 68 via, for example, a needle 72 to achieve, and maintain, a pulsatile blood concentration thereof in a subject of between about 50 and about 350 pg/ml, preferably between about 100 and about 200 pg/ml, and most preferably between about 150 pg/ml. In another embodiment, the blood concentration of the PTH[1-34]NH$_2$ in the patient is raised to its preferred level by no later than seven days following the performance of step 110. As is well understood by those skilled in the art, an appropriate dosage of PTH[1-34]NH$_2$ is determined to achieve the desired blood concentrations. In the case of injecting formulations thereof via a needle, the dosage can, though need not necessarily be, in the range of between about 10 to about 200 micrograms ("µg"), given once per day, more preferably between about 20 and about 100 µg per dose and more preferably between about 20 and about 50 µg per dose, or most preferably between about 20 and about 40 µg per dose given once per day. Moreover, as would be well understood by one having ordinary skill in this art, dosage levels of injectable formulations comprising bone augmentation agents other than [1-34]NH$_2$, which are described in further detail below, would be consistent with those noted herein. If desired, PTH [1-34]OH could also be used in an identical fashion to that described above.

Figure 5:
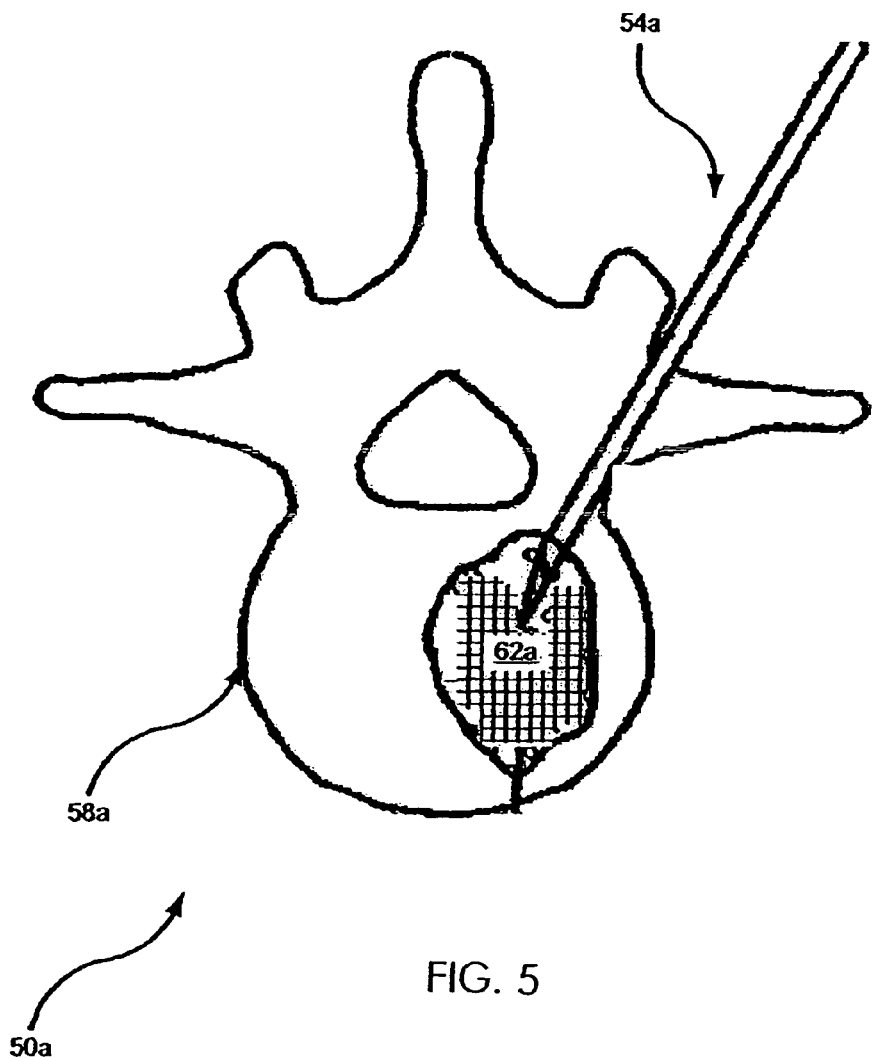
FIG. 5 is a representation of an axial view of a vertebra with an osteoporosis, wherein the vertebra is undergoing the administration of a biocompatible matrix slurry, in the performance of one of the steps identified in FIG. 2, in accordance with an alternate embodiment of the invention. In this instance, there is residual cancellous bone that will respond to the combined effects of mechanically inducing an increase in osteoblast activity, e.g., through an irrigation of at least a portion of the marrow cavity, coupled with administration of an anabolic agent, but for the regions lacking trabecular integrity the inclusion of the biocompatible material will fill in the gaps and provide the necessary framework for persistent new bone growth.

Alternate methodologies for implementing method 100 are additionally contemplated as being included within the scope of the present invention. Referring now to FIG. 5, a vertebra is indicated generally at 50a. Vertebra 50a also has an osteoporotic fracture and exemplifies one type of bone (a vertebra) and a corresponding condition (fracture) that can be treated using method 100. However, in this embodiment, to treat vertebra 50a using method 100, step 110 and step 120 are performed substantially simultaneously. FIG. 5 shows an enhanced or derivatized bone cement 62a. FIG. 2 shows a vertebroplasty needle 54a inserted along a transpedicular approach with the tip of needle 54a positioned within the vertebral body 58a. Needle 54a is also shown expressing the enhanced bone cement 62a within vertebral body 58a.

One example of the embodiment described hereinabove includes a method of treating an osteoporotic fracture in the body of an individual in need thereof wherein a biologically active bone cement (hereinafter also referred to as, a "biologic material") is delivered into an inner portion of the bone and an orally administered bone augmentation agent is used to assist integration of the cement from its injected state into a material that is akin to normal native bone by promoting bony growth on, in and/or around the particles of the cement such that the additional bone thus formed is caused to grow more rapidly, with a markedly lesser degree of resorption that methods relying upon either a bone augmentation agent or a cement used by itself.

Another example includes a method of treating an osteoporotic fracture in the body of an individual in need thereof wherein a biologic material is delivered into the bone and a nasally administered augmentation agent is used to assist integration and transformation of the biologic material from the injected state into a material that is akin to normal native bone as described above. Still another example of this embodiment includes a method of treating an osteoporotic fracture in the body of an individual in need thereof wherein a biologic material is delivered into the bone and a transdermally administered augmentation agent is used to assist in the integration and transformation of said biologic material from its injected state into a material that is akin to normal native bone.

An additional example involves a method of treating an osteoporotic fracture in the body of an individual in need thereof wherein a biologic material is delivered into the bone and an injected augmentation agent is used to assist its integration and transformation from its injected state into a material that is akin to normal native bone.

A still further example of this embodiment includes a method of treating an osteoporotic fracture in the body of an individual in need thereof wherein a biologic material is delivered into the bone and parathyroid hormone ("PTH") is used to assist in the integration and transformation of the biologic material from its injected state into a material that is akin to normal native bone.

Another example includes a method of treating an osteoporotic fracture in the body of an individual in need thereof wherein a biologic material is delivered into the bone and recombinant parathyroid hormone ("rhPTH") is used to assist its integration and transformation from its injected state into a material that is akin to normal native bone.

A further example of this embodiment of the invention includes a method of treating an osteoporotic fracture in the body of an individual in need thereof wherein a biologic material is delivered into the bone and calcitonin is used to assist its integration and transformation from its injected state into a material that is akin to normal native bone.

Still another example of this embodiment includes a method of treating an osteoporotic fracture in the body of an individual in need thereof wherein a biologic material is delivered into the bone and growth hormone is used to assist its integration and transformation from its injected state into a material that is akin to normal native bone.

An additional example includes a method of treating an osteoporotic fracture in the body of an individual in need thereof wherein a biologic material is delivered into the bone and insulin related growth factor is used to assist its integration and transformation from its injected state into a material that is akin to normal native bone. A still further example includes a method of treating an osteoporotic fracture in the body of an individual in need thereof wherein a bone cement composed of Calcium phosphate is delivered into the bone and a integration stimulant used to assist its integration and transformation from its injected state into a material that is akin to normal native bone.

Another example includes a method of treating an osteoporotic fracture in the body of an individual in need thereof wherein a bone cement composed of Calcium hydroxyapatite is delivered into the bone and an integration stimulant used to assist its integration and transformation from its injected state into a material that is akin to normal native bone.

Still another example of the invention includes a method of treating an osteoporotic fracture in the body of an individual in need thereof wherein a bone cement composed of Calcium sulphate is delivered into the bone and an integration stimulant used to assist its integration and transformation from its injected state into a material that is akin to normal native bone.

Another example includes a method of treating an osteoporotic fracture in the body of an individual in need thereof wherein a bone cement composed of Calcium aluminate is delivered into the bone and an integration stimulant used to assist its integration and trans formation from its injected state into a material that is akin to normal native bone.

An additional example of this embodiment of the invention includes a method of treating an osteoporotic fracture in the body of an individual in need thereof where a bone cement composed of bone morphogenic protein is delivered into the bone and a integration stimulant used to assist its integration and transformation from its injected state into a material that is akin to normal native bone.

Another example includes a method of treating a vertebral fracture in an individual in need thereof using cement that has an insulin related growth factor ("IGF") embedded therein, and which is delivered into the vertebrae. The method also includes administering calcitonin or PTH or other bone augmentation accelerant using any suitable delivery mechanism, such as orally, nasally, injection, transdermally etc.

Still another example includes a method of treating an osteoporotic fracture in the body of an individual in need thereof wherein a biologic material is delivered into the bone and recombinant parathyroid hormone ("rhPTH") is also delivered into the bone with the cement as an accelerant of local bone growth and cement integration and transformation from its injected state into a material that is akin to normal native bone.

An additional example of this embodiment of the invention includes a method of treating an osteoporotic fracture in the body of an individual in need thereof wherein a biologic material is delivered into the bone and recombinant parathyroid hormone ("rhPTH") and Insulin related growth factor are also delivered into the bone with the cement as an accelerant of local bone growth and cement integration and transformation from its injected state into a material that is akin to normal native bone.

Another example includes a method of treating an osteoporotic fracture in the body of an individual in need thereof where a biologic material is delivered into the bone and recombinant parathyroid hormone ("rhPTH") and Insulin related growth factor are also delivered into the bone with the cement as an accelerant of local bone growth and cement integration and transformation from its injected state into a material that is akin to normal native bone. At the same time Oral/IV or some other method of systemic bone anabolic stimulant is delivered to the patient for a broader increase in global bone density.

It should be understood that the above-described examples of the invention may include an additional step altering the contents of the bone marrow cavities in the bones so treated so as to remove all or a portion of the stromal cells from the cavity. The administration of the biocompatible material may serve this purpose by forcing the cells from the marrow cavity, or else an alternate method, such as irrigation, may instead be used for the identical purpose.

As shown, for example, in FIG. 6A, the results for bone formation in the femurs receiving a biocompatible matrix material and subsequently treated with PTH are markedly greater than for buffer (PBS) alone. These results demonstrate that the combination of BMX with a biocompatible matrix will foster continuing bone augmentation, and that the addition of PTH further improves this response.

Figure 6B:
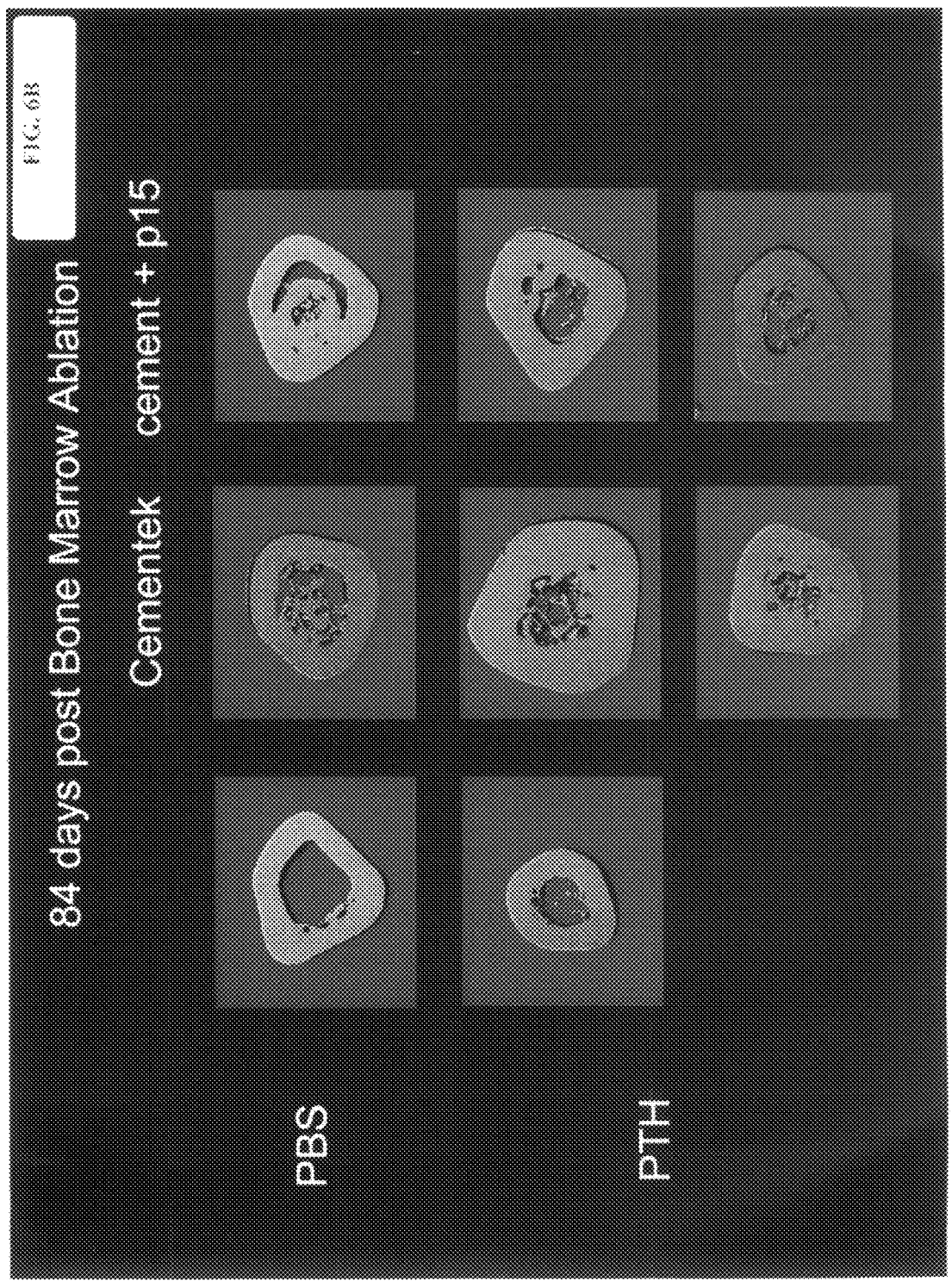
FIG. 6B depicts the results obtained from the same groups of animals reported in FIG. 6A using the Micro-CT imaging technique. This imaging technique provides a high resolution analysis of the femoral shaft marrow cavity from the BMX+ PBS or PBX+PTH treatments, compared with femurs that had biocompatible materials (Cementek or Pepgen-15) injected into the bone marrow cavity following the step (e.g., ablation) resulting in the inducement of increased osteoblast activity.

Furthermore, as shown in FIG. 6B, BMX+PTH 1-34 $NH_2$ and either biocompatible material yielded better results than the use of biocompatible material alone following BMX. The results confirm the observations obtained with the use of calcein labeling as shown in FIG. 1A.

Figure 7A:
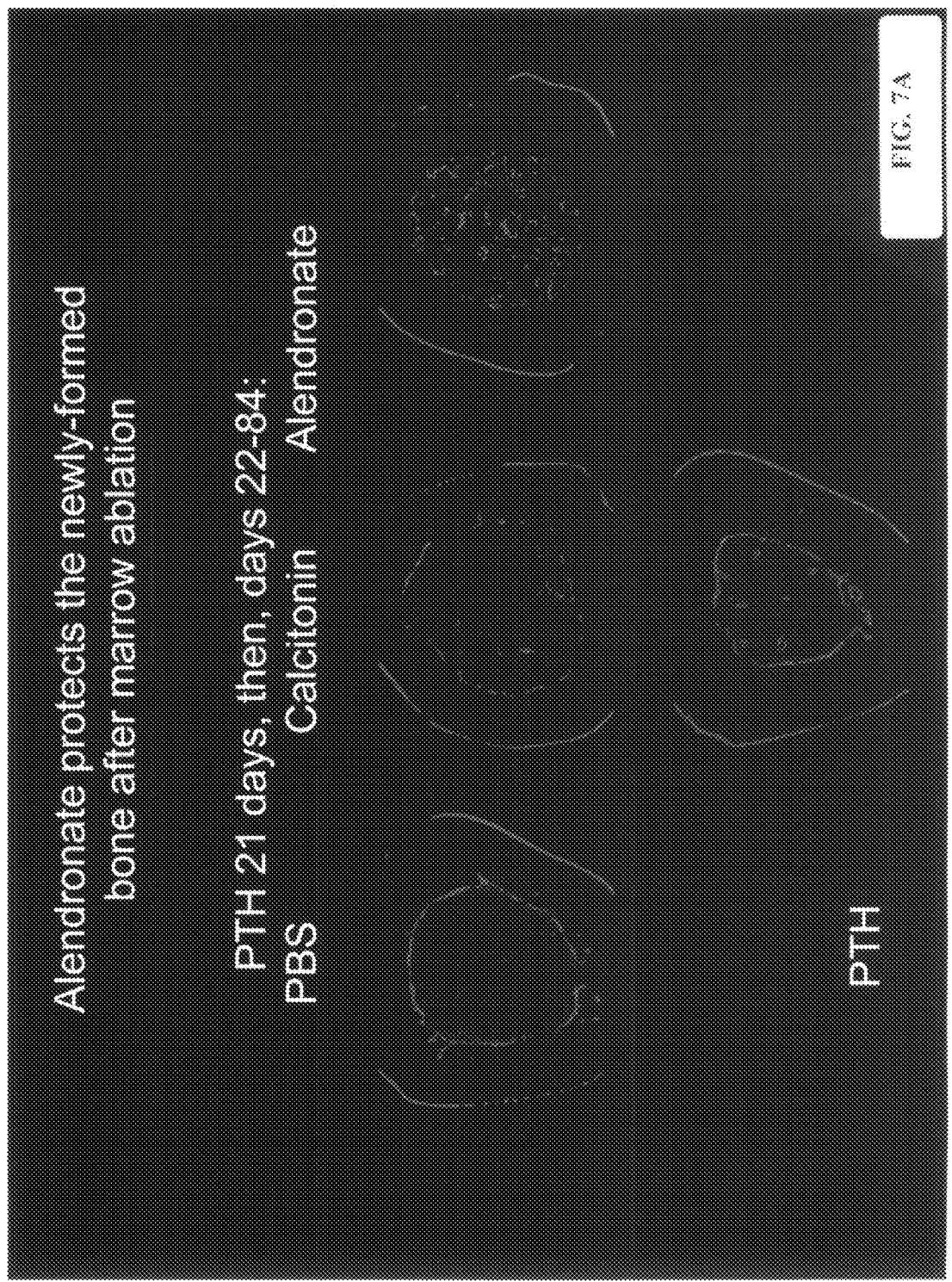

FIG. 7A illustrates that bone formed in the marrow cavity in response to bone marrow ablation (BMX) followed by 21 day treatment with PTH, is protected by treatment with calcitonin or alendronate given for the next 63 days, as illustrated by the fluorescent signal from calcein that has been incorporated into the mineralizing bone. Alendronate is a powerful anti-resorptive agent and, at the dose administered, it had a greater protective effect on the newly synthesized bone. By contrast, the ablated marrow cavity of femurs from rats treated for 84 days with PTH contains a minimum amount of fluorescent label. Calcein was injected on days 9, 8, 2 and 1 before sacrifice of the animals.

Furthermore, calcitonin and alendronate protect the bone that forms in response to marrow ablation (BMX) and 21 day treatment with PTH. As shown in FIG. 7A, the bone formed in the marrow cavity in response to marrow ablation followed by 21 day treatment with PTH is protected by calcitonin or alendronate given for the next 63 days, as demonstrated by the fluorescent signal from calcien that has been incorporated into mineralizing bone. By contrast, the ablated marrow cavity of femurs from rats treated for 84 days with PTH no longer contains fluorescent labels.

Furthermore, FIG. 7B illustrates the results obtained by Micro-CT analysis of the bone formed in the marrow cavity in response to marrow ablation followed by 21 day treatment with PTH followed by subsequent treatment with either of the anti-resorptive drugs calcitonin or alendronate, for an additional 63 days. Calcitonin, and to a greater extent, alendronate, protects the bone that forms in response to marrow ablation and 21 day treatment with PTH. By contrast, the ablated marrow cavity of the diaphysis of femurs from rats treated for 84 days with PTH no longer contains radio-dense bone. These results confirm that in anatomic regions lacking a cancellous network of trabecular bone, continuous treatment with PTH results in bone resorption. However, administration of bisphosphonates can preserve the newly formed bone located at such a site.

In a preferred embodiment, the method of the invention is utilized with a human subject. However, the invention additionally comprises veterinary applications.

In a further alternate embodiment to those heretofore set forth, the invention includes an additional step of mechanically inducing an increase in osteoblast activity within the subject to be treated, which inducement is carried out in conjunction with the introduction of a biocompatible material such as a bone cement and the administration of a bone augmentation agent, such as a bone anabolic agent, to said subject as described above. The various steps may be performed in any order, but in sufficient time proximity that an elevated concentration of the at least one bone augmentation agent in the bloodstream of the subject and the mechanically induced increase in osteoblast activity in said subject at least partially overlaps. In a further, optional, step an antiresorptive agent may be administered to the subject for a duration and at a concentration sufficient to further reduce resorption of the bone formed due to the synergistic interaction among the various method steps. An additional factor preventing such resorption and thus preserving the additional bone growth achieved through the use of the method of the invention is the presence of the bone cement, which acts as a 'scaffold' or support to permit further growth extending therefrom. Once an adequate amount of bone has been formed an anti-resorptive agent can be administered to protect the bone that has been synthesized.

The mechanical inducement may be, but is not necessarily, achieved through the use of a method which comprises mechanically altering the contents of a bone marrow cavity located within the bone where it is desired to foster and preserve such additional bony growth. Various methods for achieving such an alteration of the bone marrow cavity contents are described below.

Inducement of bone growth may include, for example, generating new or additional bone at locations where such bone growth is not presently taking place and/or stimulating the growth (i.e., increasing the rapidity thereof) of bone which is already in the process of formation. Without being bound in any way by theory, applicants believe that the inducement of bone growth takes place due to the combined effects of (1) the mechanical inducement of osteoblast activity in the subject coupled with (2) an elevation in the blood concentration of at least one bone anabolic agent therein. As used throughout this description, the bone described as being formed by the process of the invention is not limited solely to trabecular bone and should also be taken to include any one or more of the following additional 'types' of bone: compact, cortical and/or lamellar bone.

Mechanical inducement of an increase in osteoblast activity may be obtained, in a preferred embodiment of the invention, by a process of bone marrow irrigation and ablation. Again, without being bound in any way by theory, applicants believe that the bone marrow irrigation or mechanical process leads to the formation of a blood clot within the bone marrow cavity which, through a cascade of biochemical reactions, contributes to increasing osteoblast activity in the subject.

In an another embodiment, the increased osteoblast activity may alternately be obtained by coupling the mechanical inducement with an additional form of inducement such as biochemical inducement. Such biochemical inducement may be obtained by administering to the subject, for example, a quantity of a blood factor such as Factor ("F") VII, fibrinogen or fibrin, Factor VIIa or a combination thereof. Following tissue or vascular injury clotting is initiated by the binding of plasma FVII/FVIIa to tissue factor (tissue thromboplastin). This complex (FVII/FVIIa+Thromboplastin) initiates a sequence of events which leads to activation of the coagulation cascade ultimately leading to fibrin deposition and platelet activation. This complex sequence of events may contribute in part to the stimulation of osteoblasts in the bone marrow. Factors VII and VIIa are commercially available from, for example, Novo Nordisk.

The increase in osteoblast activity obtained with the use of the method of the invention may be due to a variety of factors including, but not necessarily limited to: (1) osteoblast differentiation, i.e., the production of additional osteoblasts, (2) increasing the activity and/or effectiveness of osteoblasts which are already present in inducing bone formation in the subject, and (3) a combination thereof. In a preferred embodiment of the invention, the increase in osteoblast activity would include all of the above-noted functions.

In one embodiment of the invention the method additionally comprises "targeting" one or more specific bones of the subject for inducement of bone growth. This targeting is accomplished by mechanically altering the contents of a bone marrow cavity within each targeted bone so as to induce the increased osteoblast activity therein.

The method of the invention is thus useful not only for bone repair, i.e., as in the case of a bone fracture due to trauma, but also for strengthening bone in a site-specific manner in the case of individuals shown by Dual Energy X-Ray Absorptiometry ("DEXA") or other techniques to require an increase in bone mass and/or density to prevent bone fractures (e.g., such as those afflicted with osteoporosis), or who suffer due to bone weakness from chronic pain attributable to conditions such as vertebral crush. Moreover, the method of the invention additionally serves to provide (and retain) new bone needed to serve as an anchor for prostheses such as artificial hips, knees and shoulders and/or for implants such as dental implants. The new bone growth can be targeted to bones at risk of fracture to improve strength and thereby reduce the risk of fracture.

In one embodiment of the invention, the bone anabolic agent may be administered to the subject contemporaneous with the mechanical inducement of osteoblast activity (whether by increased osteoblast formation and/or by increased bone formation by pre-existing osteoblasts), which mechanical inducement may be achieved, e.g., by alteration of the bone marrow cavity. In preferred embodiments, marrow and/or other components of the marrow cavity is/are removed under pressure (e.g., by altering the relative pressure within versus without the marrow cavity), e.g., by irrigating the cavity and removing the stromal cells.

In another embodiment the bone anabolic agent is administered subsequent to such mechanical inducement. In another embodiment the bone anabolic agent may be administered prior to mechanical inducement such that elevated levels of bone anabolic agent are already present at the time of mechanical inducement, which levels may then be maintained or continued intermittently for an extended period thereafter.

As indicated in the discussion above, the bone anabolic agent may be administered orally, intravenously, intramuscularly, subcutaneously, via implant, transmucosally, transdermally, rectally, nasally, by depot injection or by inhalation and pulmonary absorption. In another embodiment the bone anabolic agent may be administered once as a time release formulation, a plurality of times, or over one or more extended periods. It is preferred that elevated blood levels of the anabolic agent be maintained at least intermittently for between about 14-365 days, and more preferably for between about 30-180 days, post-mechanical induction. Intermittent administration of parathyroid hormone, e.g., PTH[1-34]-$NH_2$, could occur once daily or once weekly resulting in peaks of blood concentration that return to baseline levels between doses, but nevertheless result in periodic elevated blood levels of a bone anabolic agent in a manner that overlaps the elevated osteoblast activity that is initially induced mechanically, although thereafter sustained, at least in part, by the anabolic agent.

In an additional embodiment the anabolic agent is selected from the group consisting of a parathyroid hormone (PTH), anabolic Vitamin D analogs, a low-density lipoprotein receptor-related protein 5 (LRP5) activator, or an inhibitor of sclerostin binding to LRP5, an activator of non-genomic estrogen-like signaling (ANGELS), a bone morphogenic protein (BMP), an insulin-like growth factor (IGF), a fibroblast growth factor (FGF), sclerostin, leptin, a prostaglandin, a statin, strontium, a growth hormone, a growth hormone releasing factor (GHRF), hepatocyte growth factor (HGF), calcitonin gene related peptide (CGRP), parathyroid hormone related peptide (PTHrP), transforming growth factor (TGF)-PGE-2 and stable analogs thereof and combinations thereof. As used herein, the term parathyroid hormone includes, but is not limited to natural parathyroid hormone, a truncate of natural parathyroid hormone, an amidated truncate of natural parathyroid hormone, an amidated natural parathyroid hormone and combinations thereof.

In one embodiment the bone anabolic agent is truncated PTH[1-34] in the free acid form. This material is commercially available in an FDA-approved pharmaceutical formulation from Eli Lilly & Co. under the trade name Forteo® (teriparatide). Other useful bone anabolic agents for use with the invention include, but are not limited to, an amidated truncate of natural parathyroid hormone, PTH[1-30]NH$_2$, PTH[1-31]NH$_2$, PTH[1-32]NH$_2$, PTH[1-33]NH$_2$, PTH[1-34]NH$_2$ and combinations thereof. In one preferred embodiment the bone anabolic agent is PTH[1-34]NH$_2$. Methods for the preparation of truncated parathyroid hormones are described in U.S. Pat. No. 6,103,495 to Mehta et al. Moreover, methodologies for amidating such truncated parathyroid hormones are provided in, for example, U.S. Pat. No. 5,789,234 to Bertelsen et al. and U.S. Pat. No. 6,319,685 to Gilligan et al. The contents of each of these patents is specifically incorporated herein by reference.

In one embodiment of the present method, a sufficient amount of the preferred truncated parathyroid hormone (see discussion above) is administered to the subject to achieve, and thereafter maintain, a pulsatile blood concentration thereof in the subject of between about 50 and 350 pg/ml, preferably between about 100 and 200 pg/ml, and most preferably about 150 pg/ml. In another embodiment, the blood concentration of the parathyroid hormone in the subject is raised to its preferred level by no later than 7 days following mechanical alteration of the contents of the bone marrow cavity. As would be well known in this art, an appropriate dosage of the PTH bone anabolic agent must be calculated to achieve the above-indicated blood concentrations. In the case of injectable formulations, for example, the dose (in pure weight of the active hormone) given to, for example, a human subject, may be that taught in the literature relating to the bone anabolic activity of these various agents. Such dose, if given by the parenteral route, may, but does not necessarily, range between about 10-200 μg, given once per day, more preferably between about 20-100 μg per dose and most preferably between about 20-50 μg per dose. Dosage levels of injectable formulations comprising bone anabolic agents other than the above-described parathyroid hormone-based agents would be consistent with the known blood levels required to evoke an anabolic response in man.

In a further embodiment of the invention the mechanical induction of osteoblast activity is accomplished by inserting, into a bone marrow cavity of a bone targeted for enhanced bone formation, an object configured or adapted to physically alter the contents of the cavity and thereby to stimulate the osteoblast activity within the cavity. In another embodiment the mechanical alteration may include removal of at least a portion of the cavity contents. A suitable method is to irrigate the bone marrow cavity with a solution to remove stromal cells. In certain embodiments the application of the biocompatible material may be used to remove bone marrow cells and, thereby, for inducing osteoblast activity.

In a still further embodiment, the method of the invention additionally comprises administering to the subject an antiresorptive agent for a time and at a concentration sufficient to substantially prevent resorption of the new bone produced due to the osteoblast activity. In one embodiment the antiresorptive agent may be administered contemporaneous with the administration of the bone anabolic agent. In another embodiment the antiresorptive agent is administered subsequent to the administration of the bone anabolic agent. In a further embodiment the administration of the antiresorptive agent may be commenced during administration of the bone anabolic agent and such administration may then be continued beyond the termination of administration of the bone anabolic agent.

In another embodiment of the invention a single agent may by administered having both bone anabolic and antiresorptive properties. Examples of such materials include, but are not limited to estrogen, strontium ranalate and selective estrogen receptor modulators (SERMS).

In an embodiment of the method of the invention the antiresorptive agent may be a calcitonin selected from the group consisting of human calcitonin, salmon calcitonin ("sCT"), eel calcitonin, elkatonin, porcine calcitonin, chicken calcitonin, calcitonin gene related peptide (CGRP) and combinations thereof. In a preferred embodiment the antiresorptive agent is salmon calcitonin. Blood levels of calcitonin, when used as the antiresorptive agent, preferably range between about 5-500 pg/ml, more preferably between about 10-250 pg/ml and most preferably 20-50 pg/ml. Moreover, human dosage levels of the subject calcitonin agents necessary to achieve the above blood levels, in the case of, e.g., injectable formulations, may be those taught in the literature relating to the use of these materials as anabolic agents. Such dose may, but does not necessarily, range between about 5-200 μg given once per day, more preferably between about 5-50 μg and most preferably 8-20 μg by weight of the pure drug, administered daily. Salmon calcitonin (sCT) administered by alternate routes, i.e., by nasal or oral administration, would require higher dosages than those discussed above.

Alternately, a variety of additional antiresorptive agents (i.e., other than the calcitonins) are useful with the method of the present invention. These include, generally, hormone replacement therapy (HRT) agents such as selective estrogen receptor modulators (SERMS), bisphosphonates, cathepsin-K inhibitors, strontium ranalate and various combinations thereof. Specific examples of additional antiresorptive agents include, but are not limited to, (1) Premarin® available from Wyeth Laboratories, which includes estrogen as the active ingredient. A typical accepted dosage is one 0.625 mg tablet daily; (2) Actonel® available from Proctor & Gamble, which includes, as its active ingredient, risedronate sodium. A typical accepted dosage is one 5 mg tablet daily or one 35 mg tablet weekly; (3) Evista® sold by Eli Lilly & Co. which includes raloxifene HCl as the active ingredient. A typical accepted dosage of this formulation is one 60 mg tablet taken daily; and (4) Fosamax® available from Merck Pharmaceuticals, which includes alendronate as the active ingredient. Typical dosages of this material are 10 mg/day or 70 mg/week. Additional bisphosphonates include Actonel® (Proctor Gamble Aventis), Ibandronate® (GSK Roche) and Zolendronate® (Novartis).

Except where otherwise noted or where apparent from the context, dosages herein refer to the weight of the active compounds unaffected by pharmaceutical excipients, diluents, carriers or other ingredients, although such other ingredients are typically included in the variety of dosage forms useful in the method of the invention. Any dosage form (i.e., capsule, tablet, injection or the like) commonly used in the pharmaceutical industry is appropriate for use herein and the terms "excipient", "diluent" or "carrier" include such non-active ingredients as are typically included, together with active ingredients, in the industry. For example, typical capsules, pills, enteric coatings, solid or liquid diluents or excipients, flavorants, preservatives, or the like are included. Moreover, it is additionally noted that with respect to all of the dosages recommended herein, the attending clinician should monitor individual patient response, and adjust the dosage accordingly.

The antiresorptive agent may be administered orally, intravenously, intramuscularly, subcutaneously, via implant, transmucosally, rectally, nasally, by depot injection, by inhalation and pulmonary absorption or transdermally. Moreover, the antiresorptive agent may be administered once, a plurality of times, or over one or more extended periods.

Although the present invention has been described in relation to particular embodiments thereof, many other variations and modifications and other uses will become apparent to those skilled in the art. The present invention, therefore, is not limited by the specific disclosure herein, but only by the claims.

What is claimed is:

1. A method for augmenting bone in a subject in need thereof, said method comprising:
   (a) mechanically inducing an increase in osteoblast activity within said subject;
   (b) installing within an interior portion of a bone within said subject where the increase in osteoblast activity has been induced a sufficient amount of a biocompatible material to form a scaffold within said bone interior, said scaffold serving as a support for formation of new bone within said interior portion; and
   (c) separately administering to said subject, at a location other than into the bone, a sufficient amount of at least one bone augmentation agent to elevate blood concentration of at least one bone anabolic agent in said subject, wherein said bone augmentation agent is systematically administered at the location other than into the bone by a method selected from the group consisting of by injection, intravenously, peroral, transdermally, trans-nasally and transrectally, and
   wherein the elevation in blood concentration of the anabolic agent in said subject and the increase in osteoblast activity therein at least partially overlap in time.

2. The method according to claim 1, wherein the biocompatible material is selected from the group consisting of biologically active bone cements, bone morphogenic proteins, polymers, fibrinogen, synthetic fibrins, collagen gels, collagen with hydroxyapatite suspensions and combinations thereof.

3. The method according to claim 2, wherein the biocompatible material is a biologically active bone cement and the bone cement is selected from the group consisting of calcium phosphate, calcium hydroxyapatite, calcium sulphate and calcium aluminate.

4. The method according to claim 1, wherein the bone augmentation agent is a bone anabolic agent.

5. The method according to claim 4, wherein the bone anabolic agent is selected from the group consisting of a parathyroid hormone (PTH), anabolic Vitamin D analogs, a low-density lipoprotein receptor-related protein 5 (LRP5) activator, or an inhibitor of sclerostin binding to LRP5, an activator of non-genomic estrogen-like signaling (ANGELS), an insulin-like growth factor (IGF), a fibroblast growth factor (FGF), leptin, a prostaglandin, a statin, strontium, a growth hormone, a growth hormone releasing factor (GHRF), hepatocyte growth factor (HGF), calcitonin gene related peptide (CGRP), parathyroid hormone related peptide (PTHrP), transforming growth factor (TGF)-β1 and combinations thereof.

6. The method according to claim 5, wherein the bone anabolic agent is a parathyroid hormone and said hormone is selected from the group consisting of a natural parathyroid hormone, a truncate of natural parathyroid hormone, an amidated truncate of natural parathyroid hormone, an amidated natural parathyroid hormone and combinations thereof.

7. The method according to claim 6, wherein a sufficient amount of said parathyroid hormone is administered to said subject to achieve a pulsatile blood concentration thereof in said subject of between about 50-350 pg/ml.

8. The method according to claim 6, wherein said sufficient amount of parathyroid hormone is from about 10 µg-10 mg pure weight of PTH hormone per dose.

9. The method according to claim 6, wherein said parathyroid hormone is administered via injection and the sufficient amount of parathyroid hormone is from about 10-200 µg per dose.

10. The method according to claim 6, wherein the bone anabolic agent is PTH[1-34] in the free acid form.

11. The method according to claim 6, wherein the bone anabolic agent is an amidated truncate of natural parathyroid hormone and said truncate is selected from the group consisting of PTH[1-30]NH2, PTH[1-31]NH2, PTH[1-32]NH2, PTH[1-33]NH2, PTH[1-34]NH2 and combinations thereof.

12. The method according to claim 1, wherein the bone augmentation agent is at least one agent that causes elevated levels of an endogenous anabolic agent within said subject.

13. The method according to claim 12, wherein the agent causing an increased expression of the endogenous bone anabolic agent within said subject is selected from the group consisting of caicilytic agents and antibodies to sclerostin.

14. The method according to claim 1, which further comprises administering to the subject an anti-resorption agent, said anti-resorptive agent being administered in an amount sufficient to substantially prevent resorption of said new bone growth.

15. The method according to claim 14, wherein the antiresorptive agent is a bisphosphonate or a calcitonin selected from the group consisting of human calcitonin, salmon calcitonin, eel calcitonin, elkatonin, porcine calcitonin, chicken calcitonin, calcitonin gene related peptide (CGRP) and combinations thereof.

16. The method according to claim 15, wherein the antiresorptive agent is salmon calcitonin and wherein the salmon calcitonin is administered to said subject in an amount calculated to achieve a substantially continuous blood concentration thereof of between about 5-500 pg/ml.

17. The method according to claim 16, wherein the amount of salmon calcitonin is from about 5 µg to 5 mg pure weight of the calcitonin per dose.

18. The method according to claim 16, wherein the salmon calcitonin is administered via injection and the amount of salmon calcitonin is from about 5 µg-200 µg per dose.

19. The method according to claim 1 wherein the bone augmentation agent is a parathyroid hormone and wherein blood concentration of the parathyroid hormone in said subject is raised to a level of between about 50-350 pg/ml by no later than 7 days following said mechanical inducement.

20. The method according to claim 1, additionally comprising forming a sufficient amount of additional bone in a jaw region of said subject to provide an anchor for a dental implant implanted into said jaw region.

21. The method according to claim 1, additionally comprising forming a sufficient amount of additional bone in one or more targeted bones of said subject to permit a prosthetic device implanted into at least one said targeted bone to be securely anchored thereto.

22. The method according to claim 1, additionally comprising forming a sufficient amount of additional bone in said subject to serve as a secure anchor for a hollow, adjustable insert anchored to said additional bone.

23. The method according to claim 1, which further comprises targeting at least one vertebra of said subject for additional bone formation and wherein a sufficient amount of bone is added to said at least one vertebra such that the subject is substantially freed from chronic pain caused due to vertebral crush.

24. The method according to claim 1, wherein additional bone is formed on at least one vertebra of said subject in an amount sufficient to stabilize said at least one vertebra due to strengthening thereof.

25. The method according to claim 1, wherein the biocompatible material is administered via an injection into a location selected from the group consisting of the proximal femoral, the hip, the distal radius, the proximal humerus, the calcaneus, the ribs, the tibia and the sacrum.

26. The method according to claim 1, wherein the bone augmentation agent is administered in a manner selected from the group consisting of orally, nasally, transdermally, rectally, subcutaneously and intravenously.

* * * * *